US011391689B2

(12) United States Patent
Nakayama et al.

(10) Patent No.: US 11,391,689 B2
(45) Date of Patent: *Jul. 19, 2022

(54) GAS SENSOR

(71) Applicant: NGK INSULATORS, LTD., Aichi (JP)

(72) Inventors: Yuki Nakayama, Nagoya (JP); Shota Kageyama, Nagoya (JP); Yusuke Fujii, Nagoya (JP); Kei Kosaka, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 340 days.

This patent is subject to a terminal disclaimer.

(21) Appl. No.: 16/669,556

(22) Filed: Oct. 31, 2019

(65) Prior Publication Data

US 2020/0064301 A1 Feb. 27, 2020

Related U.S. Application Data

(63) Continuation of application No. PCT/JP2019/001867, filed on Jan. 22, 2019.

(30) Foreign Application Priority Data

Feb. 6, 2018 (JP) .............................. JP2018-019446

(51) Int. Cl.
G01N 27/407 (2006.01)
G01N 33/00 (2006.01)

(52) U.S. Cl.
CPC ..... G01N 27/4071 (2013.01); G01N 27/4078 (2013.01); G01N 33/0016 (2013.01); G01N 33/0036 (2013.01)

(58) Field of Classification Search
CPC .......... G01N 27/4077; G01N 27/409; G01N 27/4071; G01N 33/0016; G01N 27/4078
See application file for complete search history.

(56) References Cited

U.S. PATENT DOCUMENTS 9,080,964 B2 7/2015 Otsuka
9,476,863 B2 10/2016 Sakuma
(Continued)

FOREIGN PATENT DOCUMENTS

JP 2007278945 A 10/2007
JP 2007-285961 A 11/2007
(Continued)

OTHER PUBLICATIONS

JP2012185113 machine translation (Year: 2012).*
(Continued)

*Primary Examiner* — Luan V Van
*Assistant Examiner* — Caitlyn Mingyun Sun
(74) *Attorney, Agent, or Firm* — Mattingly & Malur, PC

(57) ABSTRACT

A gas sensor includes a sensor element and one or more hollow columnar dense bodies. The sensor element includes an element main body having a side surface, a porous layer and a water-penetration reduction portion that cover at least a front end-side part of the side surface. The water-penetration reduction portion disposed on the side surface so as to divide the porous layer an overlap length W that is the length of a continuous overlap between a range in which the water-penetration reduction portion is present in the longitudinal direction and a range in which inner peripheral surfaces of the one or more dense bodies are present in the longitudinal direction being 0.5 mm or more, the water-penetration reduction portion being a gap region in which the porous layer is absent, the water-penetration reduction portion reduces the capillarity of water.

6 Claims, 5 Drawing Sheets

(56) References Cited

U.S. PATENT DOCUMENTS

| | | |
|---|---|---|
| 10,161,900 B2 | 12/2018 | Ishikawa |
| 2007/0235332 A1 | 10/2007 | Sugiyama et al. |
| 2007/0246359 A1 | 10/2007 | Sugiyama et al. |
| 2009/0242404 A1 | 10/2009 | Miyashita et al. |
| 2012/0103808 A1 | 5/2012 | Igarashi et al. |
| 2012/0211362 A1 | 8/2012 | Onkawa |
| 2014/0130572 A1 | 5/2014 | Otsuka |
| 2015/0075254 A1 | 3/2015 | Sakuma |
| 2015/0114085 A1 | 4/2015 | Iwano |
| 2015/0268187 A1 | 9/2015 | Adachi et al. |
| 2015/0355142 A1 | 12/2015 | Murakami et al. |
| 2016/0054256 A1 | 2/2016 | Sakuma |
| 2016/0161445 A1* | 6/2016 | Sakakibara .......... G01N 27/419 204/424 |
| 2018/0217088 A1 | 8/2018 | Tahira et al. |
| 2018/0284055 A1 | 10/2018 | Hino |
| 2020/0049679 A1* | 2/2020 | Nakayama ......... G01N 33/0036 |

FOREIGN PATENT DOCUMENTS

| | | |
|---|---|---|
| JP | 2009-236833 A | 10/2009 |
| JP | 2009-236835 A | 10/2009 |
| JP | 2012-108104 A | 6/2012 |
| JP | 2012-242112 A | 12/2012 |
| JP | 2014-055859 A | 3/2014 |
| JP | 2015-178988 A | 10/2015 |
| JP | 2016-014659 A | 1/2016 |
| JP | 2016-065852 A | 4/2016 |
| JP | 2017-106874 A | 6/2017 |
| JP | 2018-119901 A | 8/2018 |

OTHER PUBLICATIONS

International Search Report of PCT/JP2019/001867 dated Apr. 23, 2019.
International Preliminary Report on Patentability received in corresponding International Application No. PCT/JP2019/001867 dated Aug. 20, 2020.
U.S. Appl. No. 16/669,555, filed Oct. 31, 2019.
International Preliminary Report on Patentability received in International Application No. PCT/JP2019/001849 dated Aug. 20, 2020.
Japanese Office Action received in Japanese Application No. 2019-570654 dated Nov. 10, 2020.
Japanese Notice of Opposition received in Japanese Application No. 2021-700870 dated Oct. 8, 2021.
International Search Report of PCT/JP2019/001849 dated Apr. 23, 2019.
U.S. Appl. No. 16/658,340, filed Oct. 21, 2019.

* cited by examiner

GAS SENSOR

CROSS-REFERENCE TO RELATED APPLICATION

This application is a continuation application of PCT/JP2019/001867, filed on Jan. 22, 2019, which claims the benefit of priority of Japanese Patent Application No. 2018-019446, filed on Feb. 6, 2018, the entire contents of which are incorporated herein by reference.

BACKGROUND OF THE INVENTION

1. Field of the Invention

The present invention relates to a gas sensor.

2. Description of the Related Art

Gas sensors that include a sensor element that detects the concentration of a particular gas, such as NOx, in the measurement-object gas, such as an automotive exhaust gas, are known (e.g., PTLs 1 and 2). The sensor element disclosed in PTL 1 includes a multilayer body that includes oxygen ion-conducting solid electrolyte layers stacked on top of one another. This sensor element also includes an outer pump electrode, a lead wire for the outer pump electrode, a connector electrode, and a porous protection layer, which are stacked on and above the upper surface of the multilayer body. The outer pump electrode, the lead wire for the outer pump electrode, and the connector electrodes are connected to one another in this order and are in electrical conduction with one another. The connector electrode is electrically connected to the outside. The porous protection layer covers and protects the outer pump electrode and the lead wire for the outer pump electrode. In PTL 2, the structure of a gas sensor including the above-described sensor element is described. The gas sensor described in PTL 2 includes an element-sealing member that fixes the sensor element in position. The element-sealing member includes a cylindrical main fitting and an inner cylinder in which the sensor element is disposed so as to penetrate the main fitting and the inner cylinder and a plurality of supports and a plurality of compacts which are disposed inside the main fitting and the inner cylinder and in which the sensor element is disposed so as to penetrate the supports and the compacts.

CITATION LIST

Patent Literature

PTL 1: Japanese Unexamined Patent Application Publication No. 2016-014659
PTL 2: Japanese Unexamined Patent Application Publication No. 2015-178988

SUMMARY OF THE INVENTION

When a porous layer similar to the porous protection layer described in PTL 1 is present on the surface of the sensor element, the moisture contained in an exhaust gas may move inside the porous layer by capillarity. As a result, the moisture may reach the connector electrode. In such a case, water and the components dissolved in water, such as sulfuric acid, cause rusting and corrosion of the connector electrode and a short circuit between the connector electrodes.

The present invention was made in order to address the above issues. An object of the present invention is to prevent the moisture from reaching the connector electrodes.

The present invention employs the following structures in order to achieve the object.

The gas sensor according to the present invention includes:

a sensor element; a cylindrical body made of a metal, the cylindrical body having a through-hole through which the sensor element penetrates an inside of the cylindrical body in an axial direction of the cylindrical body; one or more compacts disposed in the through-hole, the compacts filling a gap between an inner peripheral surface of the through-hole and the sensor element; and one or more hollow columnar dense bodies having a porosity of less than 10%, the dense bodies being disposed in the through-hole, the dense bodies being penetrated by the sensor element, the dense bodies pressing the compacts in the axial direction.

The sensor element includes:

a long-length element main body including front and rear ends and one or more side surfaces, the front and rear ends being ends of the element main body in a longitudinal direction of the element main body, the one or more side surfaces being surfaces extending in the longitudinal direction, a detection unit including a plurality of electrodes disposed in the front end-side part of the element main body, the detection unit detecting the concentration of a particular gas in the measurement-object gas, one or more connector electrodes disposed on the rear end-side part of any of the one or more side surfaces, the connector electrodes being in electrical conduction with the outside, a porous layer that covers at least the front end-side part of the side surface on which the connector electrodes are disposed, the porous layer having a porosity of 10% or more, and a water-penetration reduction portion disposed on the side surface so as to divide the porous layer in the longitudinal direction, the water-penetration reduction portion being located closer to the front end than the connector electrodes, an overlap length W that is the length of a continuous overlap between a range in which the water-penetration reduction portion is present in the longitudinal direction and a range in which inner peripheral surfaces of the one or more dense bodies are present in the longitudinal direction being 0.5 mm or more, the water-penetration reduction portion including a gap region in which the porous layer is absent, the water-penetration reduction portion reducing the capillarity of water in the longitudinal direction.

In the above-described gas sensor, the connector electrodes are disposed on a rear end-side part of any of the one or more side surfaces of the element main body, and the porous layer is arranged to cover at least the front end-side part of the side surface. Furthermore, the sensor element includes the water-penetration reduction portion disposed on the side surface so as to divide the porous layer in the longitudinal direction. The water-penetration reduction portion is located closer to the front end than the connector electrode. Therefore, even when the front end-part of the element main body, in which a plurality of electrodes constituting the detection unit are present, is exposed to the measurement-object gas and the moisture contained in the measurement-object gas moves inside the porous layer toward the rear end of the element main body by capillarity, the moisture reaches the water-penetration reduction portion before reaching the connector electrodes. In the water-penetration reduction portion, which is the gap region in which the porous layer is absent, the capillarity of water in the longitudinal direction of the element main body is not likely to occur, unlike in the porous layer. Therefore, the likelihood of the moisture passing through the water-penetration reduction portion is low. Furthermore, in the gas sensor according to the present invention, the overlap length W that is the length of a continuous overlap between the range in which the water-penetration reduction portion is present in the longitudinal direction of the sensor element and the range in which inner peripheral surfaces of the one or more dense bodies are present in the longitudinal direction is 0.5 mm or more. The compacts and the dense bodies are interposed between the cylindrical body and the sensor element. While the likelihood of the moisture passing through the dense bodies is low since the dense bodies have a porosity of less than 10%, the moisture can move inside the compacts, which absorb water, as well as inside the porous layer. Therefore, if the overlap length W is 0 mm, that is, for example, the water-penetration reduction portion is disposed at only the position that is the same, in the longitudinal direction of the sensor element, as the positions at which the compacts are disposed, the moisture may bypass the water-penetration reduction portion as a result of passing through the compacts and move into the rear end-side part. In contrast, in the gas sensor according to the present invention, since the overlap length W is 0.5 mm or more, the region that reduces the likelihood of the moisture moving inside the compacts and bypassing the water-penetration reduction portion is present over a sufficiently large distance and, consequently, the movement of the moisture due to the bypass can be suppressed to a sufficient degree. By the above-described mechanisms, the water-penetration reduction portion reduces the likelihood of the moisture that moves inside the porous layer passing through the water-penetration reduction portion and the likelihood of the moisture bypassing the water-penetration reduction portion as a result of passing through the compacts. Consequently, the above-described gas sensor reduces the likelihood of the moisture moving into the rear end-side part of the sensor element across the water-penetration reduction portion and reaching the connector electrodes. Since the length L of the water-penetration reduction portion in the longitudinal direction is always equal to or larger than the overlap length W, the length L is also 0.5 mm or more. In this case, the overlap length W may be 5 mm or more. The overlap length W may be 20 mm or less. The porous body may cover at least a part of the side surface on which the connector electrodes are disposed which extends from the front end of the side surface to the rear of the water-penetration reduction portion, the part excluding the region in which the water-penetration reduction portion is present.

In the gas sensor according to the present invention, the length L of the water-penetration reduction portion in the longitudinal direction may be 1 mm or less. In such a case, since the length L of the water-penetration reduction portion is relatively small, the area of a part of the side surface of the element main body which is exposed to the outside (the part that is not covered with the porous layer) can be reduced.

In the gas sensor according to the present invention, the height H of the water-penetration reduction portion which is the distance from the side surface to the inner peripheral surfaces of the dense bodies may be 50 µm or more. In such a case, the capillarity in the gap between the side surface and the inner peripheral surfaces of the dense bodies due to the small distance between the side surface of the element main body on which the water-penetration reduction portion is disposed and the dense bodies can be further reduced. The height H may be 500 µm or less.

In the gas sensor according to the present invention, the sensor element may further include an outer lead portion disposed on the side surface on which the connector electrodes are disposed, the outer lead portion providing conduction between any of the electrodes and the connector electrodes, and the porous layer may cover at least a part of the outer lead portion. This enables at least a part of the outer lead portion to be protected with the porous layer. In the case where the outer lead portion is protected with the porous layer, the porous layer is likely to be disposed at a position close to the connector electrodes and, therefore, it is meaningful to apply the present invention to such a gas sensor.

In the above case, the porous layer may cover the entirety of the outer lead portion. Alternatively, the porous layer may cover the entirety of the part of the outer lead portion on which the water-penetration reduction portion is not present. The gas sensor according to the present invention may include an outer electrode that is one of the electrodes included in the detection unit, the outer electrode being in conduction with the connector electrodes via the outer lead portion and disposed on the side surface on which the connector electrodes are disposed. In such a case, the porous layer may cover the outer electrode.

In the gas sensor according to the present invention, the porous layer may cover at least a part of the side surface on which the connector electrodes are disposed which extends from the front end of the side surface to the front end-side edges of the connector electrodes, the part excluding the region in which the water-penetration reduction portion is present.

In the gas sensor according to the present invention, the element main body may have a rectangular cuboid shape and four side surfaces that are surfaces extending in the longitudinal direction, one or more connector electrodes may be disposed on each of first and second side surfaces of the four side surfaces, the first and second side surfaces facing each other, the porous layer may cover each of the first and second side surfaces, and the water-penetration reduction portion may be disposed on each of the first and second side surfaces. In the above case, the element main body may be a multilayer body constituted by a plurality of layers stacked on top of one another, and the first and second side surfaces may be the upper and lower surfaces of the element main body when the direction in which the layers are stacked is considered the top-to-bottom direction.

DETAILED DESCRIPTION OF THE INVENTION

Figure 1:
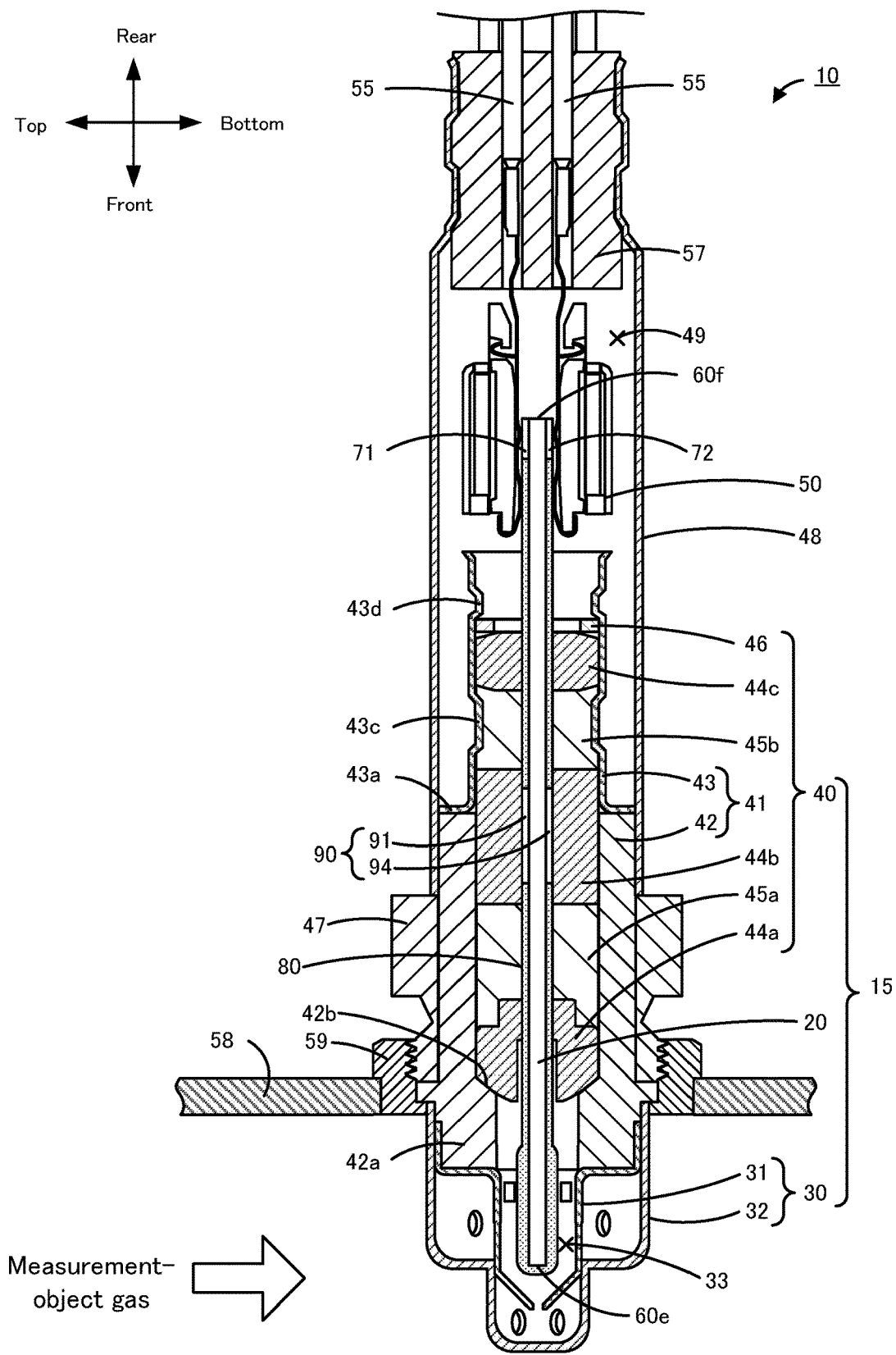
FIG. 1 is a longitudinal cross-sectional view of a gas sensor 10 attached to a pipe 58.
Figure 2:
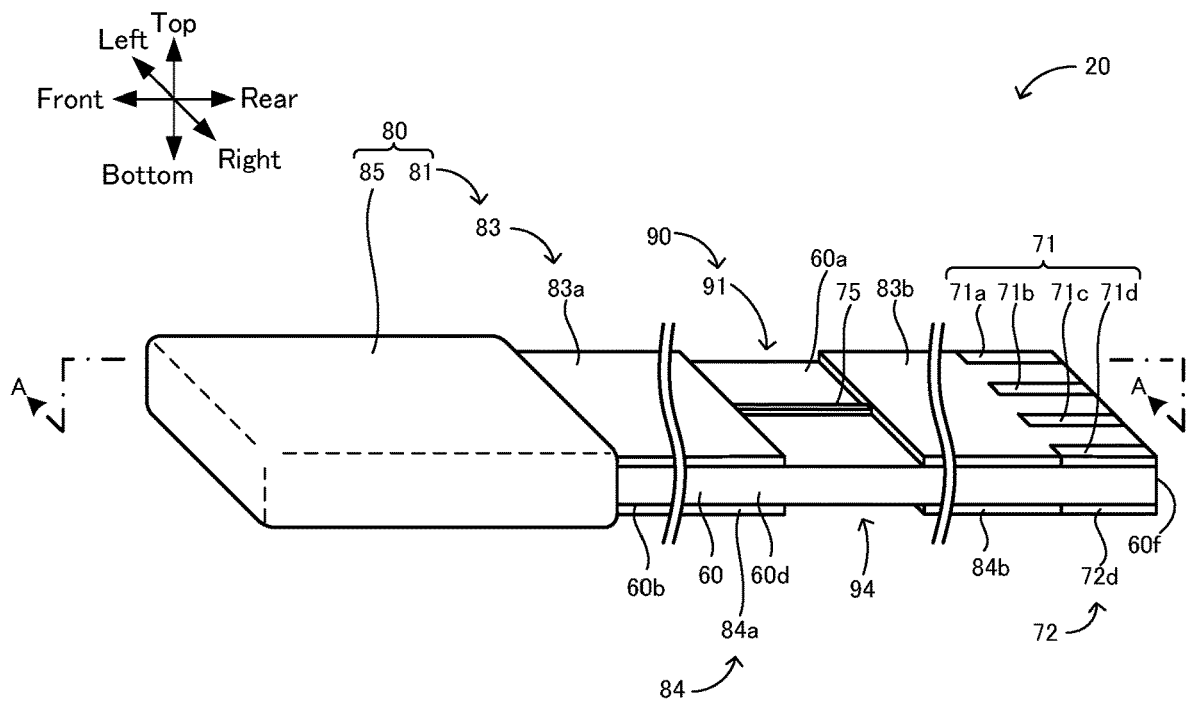
FIG. 2 is a perspective view of a sensor element 20.
Figure 3:
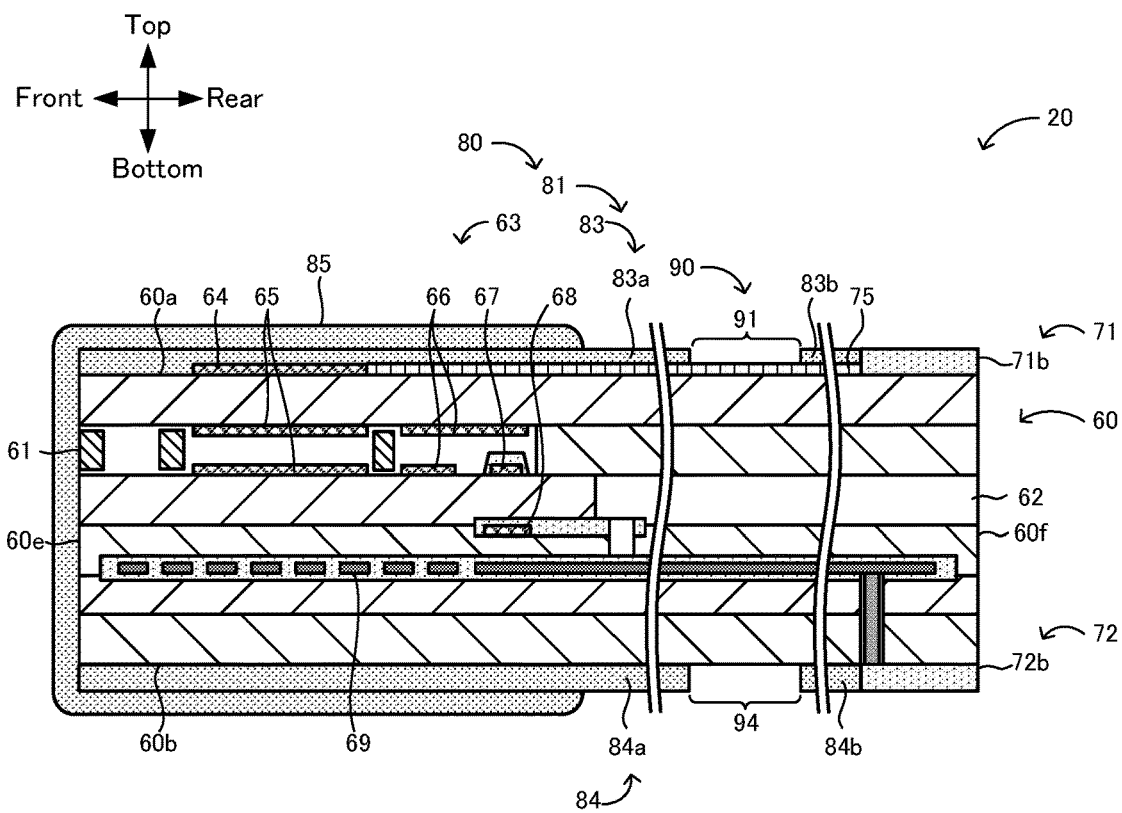
FIG. 3 is a cross-sectional view taken along the line A-A in FIG. 2.
Figure 4:
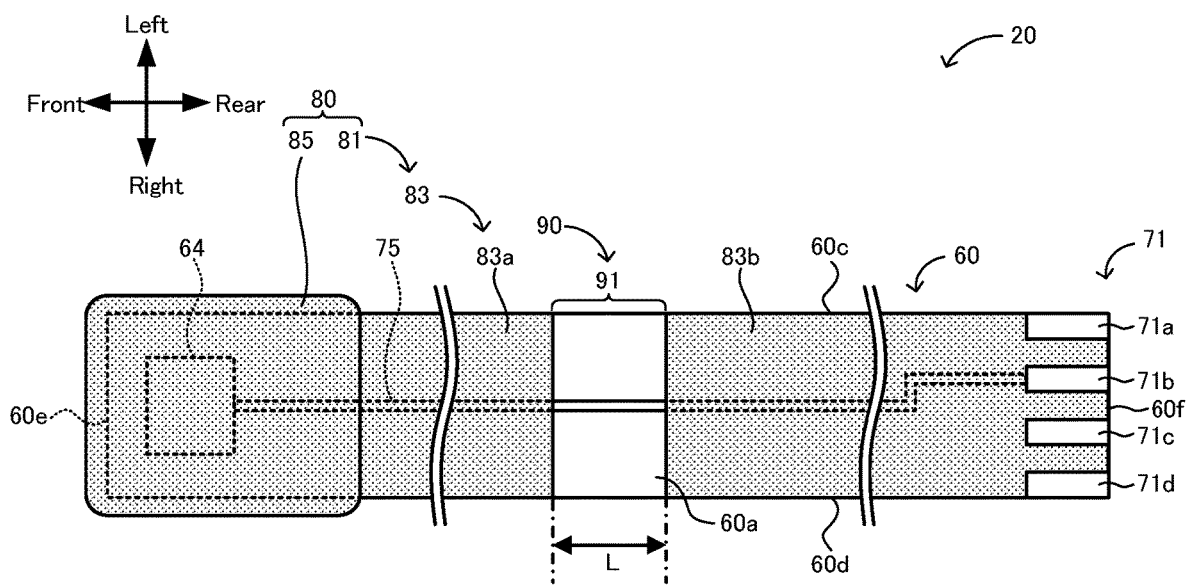
FIG. 4 is a top view of a sensor element 20.
Figure 5:
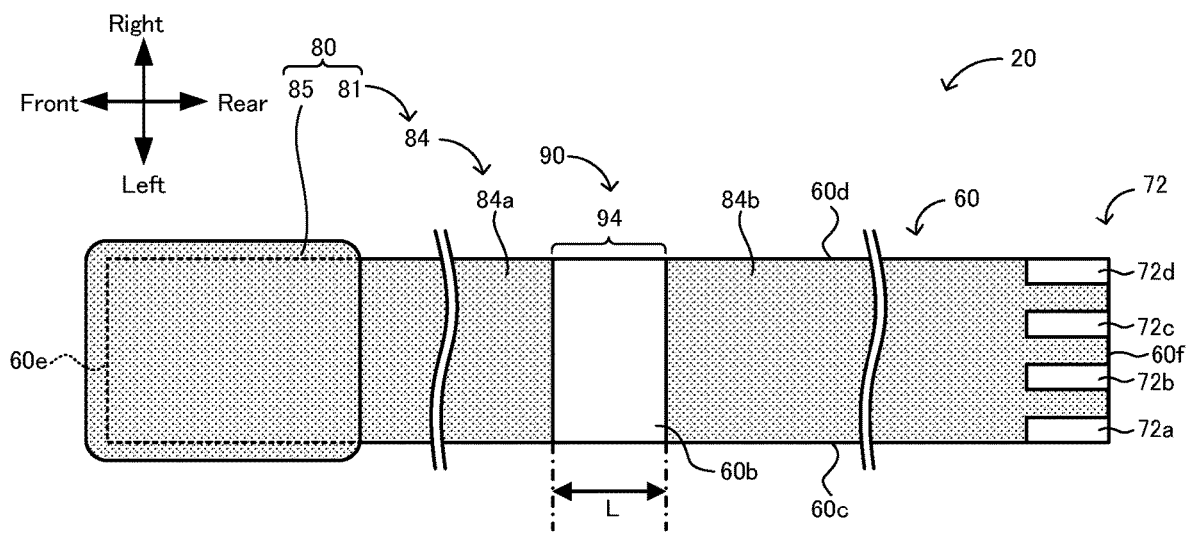
FIG. 5 is a bottom view of a sensor element 20.

Embodiments of the present invention are described below with reference to the attached drawings. FIG. 1 is a longitudinal cross-sectional view of a gas sensor 10 according to an embodiment of the present invention which is attached to a pipe 58. FIG. 2 is a perspective view of a sensor element 20 viewed from the upper right front. FIG. 3 is a cross-sectional view taken along the line A-A in FIG. 2. FIG. 4 is a top view of the sensor element 20. FIG. 5 is a bottom view of the sensor element 20. In this embodiment, as illustrated in FIGS. 2 and 3, the longitudinal direction of the element main body 60 included in the sensor element 20 is referred to as "front-to-rear direction" (length direction), the direction in which the layers constituting the element main body 60 are stacked (thickness direction) is referred to as "top-to-bottom direction", and a direction perpendicular to the front-to-rear direction and the top-to-bottom direction is referred to as "left-to-right direction" (width direction).

As illustrated in FIG. 1, the gas sensor 10 includes an assembly 15, a nut 47, an external cylinder 48, a connector 50, lead wires 55, and a rubber stopper 57. The assembly 15 includes a sensor element 20, a protective cover 30, and an element-sealing member 40. The gas sensor 10 is attached to a pipe 58, such as an automotive exhaust gas pipe, and used for measuring the concentration of a particular gas, such as NOx or $O_2$, (particular gas concentration) in the exhaust gas, which is the gas to be analyzed. In this embodiment, the gas sensor 10 is a gas sensor that measures NOx concentration as a particular gas concentration. Among the ends (front and rear ends) of the sensor element 20 in the longitudinal direction, the front end-side part of the sensor element 20 is exposed to the measurement-object gas.

The protective cover 30 includes, as illustrated in FIG. 1, a hollow cylindrical inner protective cover 31 with a bottom which covers the front end-part of the sensor element 20 and a hollow cylindrical outer protective cover 32 with a bottom which covers the inner protective cover 31. Each of the inner and outer protective covers 31 and 32 has a plurality of holes formed therein, through which the measurement-object gas is passed. The space surrounded by the inner protective cover 31 serves as an element chamber 33. A fifth surface 60e (front end-side surface) of the sensor element 20 is located inside the element chamber 33.

The element-sealing member 40 is a member with which the sensor element 20 is sealed and fixed. The element-sealing member 40 includes a cylindrical body 41 including a main fitting 42 and an inner cylinder 43, insulators 44a to 44c (an example of the dense bodies), compacts 45a and 45b, and a metal ring 46. The sensor element 20 is located on the central axis of the element-sealing member 40 and penetrates the element-sealing member 40 in the vertical direction.

The main fitting 42 is a hollow cylindrical member made of a metal. The front-side part of the main fitting 42 is a thick-wall portion 42a having a smaller inside diameter than the rear-side part of the main fitting 42. The protective cover 30 is attached to a part of the main fitting 42 which is on the same side as the front end-side of the sensor element 20 (front-side part of the main fitting 42). The rear end of the main fitting 42 is welded to a flange portion 43a of the inner cylinder 43. A part of the inner peripheral surface of the thick-wall portion 42a serves as a bottom surface 42b, which is a stepped surface. The bottom surface 42b holds the insulator 44a such that the insulator 44a does not protrude forward. The main fitting 42 has a through-hole formed therein so as to penetrate the main fitting 42 in the axial direction (in this embodiment, the front-to-rear direction). The sensor element 20 is disposed in the through-hole so as to penetrate the through-hole.

The inner cylinder 43 is a hollow cylindrical member made of a metal and includes the flange portion 43a formed at the front end of the inner cylinder 43. The inner cylinder 43 and the main fitting 42 are coaxially fixed to each other by welding. The inner cylinder 43 includes a diameter reduction portion 43c that presses the compact 45b toward the central axis of the inner cylinder 43 and a diameter reduction portion 43d that presses the insulators 44a to 44c and the compacts 45a and 45b in the downward direction in FIG. 1 with the metal ring 46 interposed therebetween, the diameter reduction portions 43c and 43d being formed in the inner cylinder 43. The inner cylinder 43 has a through-hole formed therein so as to penetrate the inner cylinder 43 in the axial direction (in this embodiment, the front-to-rear direction). The sensor element 20 is disposed in the through-hole so as to penetrate the through-hole. The through-hole of the main fitting 42 and the through-hole of the inner cylinder 43 are communicated with each other in the axial direction and constitute the through-hole of the cylindrical body 41.

The insulators 44a to 44c and the compacts 45a and 45b are interposed between the inner peripheral surface of the through-hole of the cylindrical body 41 and the sensor element 20. The insulators 44a to 44c serve as a support for the compacts 45a and 45b. Examples of the material for the insulators 44a to 44c include ceramics, such as alumina, steatite, zirconia, spinel, cordierite, and mullite, and glass. The insulators 44a to 44c are dense members having a porosity of, for example, less than 1%. Each of the insulators 44a to 44c has a through-hole formed therein so as to penetrate the insulator in the axial direction (in this embodiment, the front-to-rear direction). The sensor element 20 is disposed in the through-hole so as to penetrate the through-hole. In this embodiment, a cross section of the through-holes of the insulators 44a to 44c which is perpendicular to the axial direction is rectangular in order to adjust to the shape of the sensor element 20. The compacts 45a and 45b are formed by, for example, molding a powder and serve as a sealing medium. Examples of the material for the compacts 45a and 45b include talc and ceramic powders, such as an alumina powder and boron nitride. The compacts 45a and 45b may include at least one of the above materials. The average size of the particles constituting the compacts 45a and 45b may be 150 to 300 μm. The compact 45a is filled between the insulators 44a and 44b and pressed by the insulators 44a and 44b as a result of both (front and rear) ends of the compact 45a in the axial direction being sandwiched therebetween. The compact 45b is filled between the insulators 44b and 44c and pressed by the insulators 44b and 44c as a result of both (front and rear) ends of the compact 45b in the axial direction being sandwiched therebetween. The insulators 44a to 44c and the compacts 45a and 45b are sandwiched between the diameter reduction portion 43d and the metal ring 46, and the bottom surface 42b of the thick-wall portion 42a of the main fitting 42 and thereby pressed in the front-to-rear direction. As a result of the compacts 45a and 45b being compressed between the cylindrical body 41 and the sensor element 20 by the pressing force applied by the diameter reduction portions 43c and 43d, the compacts 45a and 45b seal the communication between the element chamber 33 formed inside the protective cover 30 and a space 49 created inside the external cylinder 48 and fix the sensor element 20.

The nut 47 is fixed to the outer surface of the main fitting 42 coaxially with the main fitting 42. The nut 47 includes a male thread portion formed in the outer peripheral surface of the nut 47. The male thread portion is inserted into a fixing member 59, which is welded to the pipe 58 and includes a female thread portion formed in the inner peripheral surface of the fixing member 59. This enables the gas sensor 10 to be fixed to the pipe 58 while the front end-side part of the sensor element 20 of the gas sensor 10 and the protective cover 30 of the gas sensor 10 are protruded toward the inside of the pipe 58.

The external cylinder 48 is a hollow cylindrical member made of a metal and covers the inner cylinder 43, the rear end-side part of the sensor element 20, and the connector 50. The upper part of the main fitting 42 is inserted into the external cylinder 48. The lower end of the external cylinder 48 is welded to the main fitting 42. A plurality of the lead wires 55, which are connected to the connector 50, are drawn from the upper end of the external cylinder 48 to the outside. The connector 50 is in contact with upper and lower connector electrodes 71 and 72 disposed on the rear end-side parts of the surfaces of the sensor element 20 and electrically connected to the sensor element 20. The lead wires 55 are in electrical conduction with electrodes 64 to 68 and a heater 69 disposed inside the sensor element 20 via the connector 50. The gap between the external cylinder 48 and the lead wires 55 is sealed with the rubber stopper 57. The space 49 inside the external cylinder 48 is filled with a reference gas. A sixth surface 60f (rear end-side surface) of the sensor element 20 is located inside the space 49.

The sensor element 20 includes an element main body 60, a detection unit 63, a heater 69, an upper connector electrode 71, a lower connector electrode 72, a porous layer 80, and a water-penetration reduction portion 90 as illustrated in FIGS. 2 to 5. The element main body 60 includes a multilayer body constituted by a plurality of (6 layers in FIG. 3) oxygen ion-conducting solid-electrolyte layers composed of zirconia ($ZrO_2$) or the like which are stacked on top of one another. The element main body 60 has a long-length, rectangular cuboid shape, and the longitudinal direction of the element main body 60 is parallel to the front-to-rear direction. The element main body 60 has first to sixth surfaces 60a to 60f, which are the upper, lower, left, right, front, and rear outer surfaces of the element main body 60. The first to fourth surfaces 60a to 60d are surfaces that extend in the longitudinal direction of the element main body 60 and correspond to the side surfaces of the element main body 60. The fifth surface 60e is the front end-side surface of the element main body 60. The sixth surface 60f is the rear end-side surface of the element main body 60. The dimensions of the element main body 60 may be, for example, 25 mm or more and 100 mm or less long, 2 mm or more and 10 mm or less wide, and 0.5 mm or more and 5 mm or less thick. The element main body 60 includes a gas-to-be-analyzed introduction port 61 formed in the fifth surface 60e, through which the measurement-object gas is introduced into the element main body 60, and a reference gas introduction port 62 formed in the sixth surface 60f, through which a reference gas (in this embodiment, air) used as a reference for detecting the particular gas concentration is introduced into the element main body 60.

The detection unit 63 detects the concentration of a particular gas in the measurement-object gas. The detection unit 63 includes a plurality of electrodes disposed in the front end-side part of the element main body 60. In this embodiment, the detection unit 63 includes an outer electrode 64 disposed on the first surface 60a and an inner main pump electrode 65, an inner auxiliary pump electrode 66, a measurement electrode 67, and a reference electrode 68 that are disposed inside the element main body 60. The inner main pump electrode 65 and the inner auxiliary pump electrode 66 are disposed on the inner peripheral surface of a cavity formed inside the element main body 60 and have a tunnel-like structure.

Since the principle on which the detection unit 63 detects the concentration of a particular gas in the measurement-object gas is publicly known, detailed description is omitted herein. The detection unit 63 detects the particular gas concentration, for example, in the following manner. The detection unit 63 draws oxygen included in the measurement-object gas which is in the vicinity of the inner main pump electrode 65 to or from the outside (the element chamber 33) on the basis of the voltage applied between the outer electrode 64 and the inner main pump electrode 65. The detection unit 63 also draws oxygen included in the measurement-object gas which is in the vicinity of the inner auxiliary pump electrode 66 to or from the outside (the element chamber 33) on the basis of the voltage applied between the outer electrode 64 and the inner auxiliary pump electrode 66. This enables the measurement-object gas to reach a space around the measurement electrode 67 after the oxygen concentration in the gas has been adjusted to be a predetermined value. The measurement electrode 67 serves as a NOx-reducing catalyst and reduces the particular gas (NOx) included in the measurement-object gas. The detection unit 63 converts an electromotive force generated between the measurement electrode 67 and the reference electrode 68 in accordance with the oxygen concentration in the reduced gas or a current that flows between the measurement electrode 67 and the outer electrode 64 on the basis of the electromotive force into an electrical signal. The electrical signal generated by the detection unit 63 indicates the value reflective of the particular gas concentration in the measurement-object gas (the value from which the particular gas concentration can be derived) and corresponds to the value detected by the detection unit 63.

The heater 69 is an electric resistor disposed inside the element main body 60. Upon the heater 69 being fed with power from the outside, the heater 69 generates heat and heats the element main body 60. The heater 69 is capable of heating the solid-electrolyte layers constituting the element main body 60 and conserving the heat such that the temperature is adjusted to be the temperature (e.g., 800° C.) at which the solid-electrolyte layers become active.

The upper connector electrode 71 and the lower connector electrode 72 are each disposed on the rear end-side part of any of the side surfaces of the element main body 60. The upper connector electrode 71 and the lower connector electrode 72 are electrodes that enable electrical conduction between the element main body 60 and the outside. The upper and lower connector electrodes 71 and 72 are not covered with the porous layer 80 and exposed to the outside. In this embodiment, four upper connector electrodes 71a to 71d, which serve as an upper connector electrode 71, are arranged in the left-to-right direction and disposed on the rear end-side part of the first surface 60a, and four lower connector electrodes 72a to 72d, which serve as a lower connector electrode 72, are arranged in the left-to-right direction and disposed on the rear end-side part of the second surface 60b (lower surface), which is opposite to the first surface 60a (upper surface). Each of the connector electrodes 71a to 71d and 72a to 72d is in electrical conduction with any of the electrodes 64 to 68 and the heater 69 included in the detection unit 63. In this embodiment, the upper connector electrode 71a is in conduction with the measurement electrode 67; the upper connector electrode 71b is in conduction with the outer electrode 64; the upper connector electrode 71c is in conduction with the inner auxiliary pump electrode 66; the upper connector electrode 71d is in conduction with the inner main pump electrode 65; the lower connector electrodes 72a to 72c are each in conduction with the heater 69; and the lower connector electrode 72d is in conduction with the reference electrode 68. The upper connector electrode 71b and the outer electrode 64 are in conduction with each other via an outer lead wire 75 disposed on the first surface 60a (see FIGS. 3 and 4). Each of the other connector electrodes is in conduction with a corresponding one of the electrodes and the heater 69 via a lead wire, through-hole, or the like formed inside the element main body 60.

The porous layer 80 is a porous body that covers at least the front end-side parts of the side surfaces of the element main body 60 on which the upper and lower connector electrodes 71 and 72 are disposed, that is, the first and second surfaces 60a and 60b. In this embodiment, the porous layer 80 includes an inner porous layer 81 that covers the first and second surfaces 60a and 60b and an outer porous layer 85 disposed on the outer surface of the inner porous layer 81.

The inner porous layer 81 includes a first inner porous layer 83 that covers the first surface 60a and a second inner porous layer 84 that covers the second surface 60b. The first inner porous layer 83 covers the entirety of the region extending from the front end to the rear end of the first surface 60a on which the upper connector electrodes 71a to 71d are disposed, except the regions in which a first water-penetration reduction portion 91 and the upper connector electrode 71 are present (see FIGS. 2 to 4). The width of the first inner porous layer 83 in the left-to-right direction is equal to the width of the first surface 60a in the left-to-right direction. The first inner porous layer 83 covers the region that extends from the left end to the right end of the first surface 60a. The first water-penetration reduction portion 91 divides the first inner porous layer 83 into a front end-side portion 83a located on the front end-side across the first water-penetration reduction portion 91 and a rear end-side portion 83b located on the rear end-side across the first water-penetration reduction portion 91 in the longitudinal direction. The first inner porous layer 83 covers at least a part of the outer electrode 64 and at least a part of the outer lead wire 75. In this embodiment, the first inner porous layer 83 covers the entirety of the outer electrode 64 and the entirety of the part of the outer lead wire 75 on which the first water-penetration reduction portion 91 is not present as illustrated in FIGS. 3 and 4. The first inner porous layer 83 serves as, for example, a protection layer that protects the outer electrode 64 and the outer lead wire 75 from the components of the measurement-object gas, such as sulfuric acid, and suppresses the corrosion and the like of the outer electrode 64 and the outer lead wire 75.

The second inner porous layer 84 covers the entirety of the region extending from the front end to the rear end of the second surface 60b on which the lower connector electrodes 72a to 72d are disposed, except the regions in which a second water-penetration reduction portion 94 and the lower connector electrode 72 are present (see FIGS. 2, 3, and 5). The width of the second inner porous layer 84 in the left-to-right direction is equal to the width of the second surface 60b in the left-to-right direction. The second inner porous layer 84 covers the region that extends from the left end to the right end of the second surface 60b. The second water-penetration reduction portion 94 divides the second inner porous layer 84 into a front end-side portion 84a located on the front end-side across the second water-penetration reduction portion 94 and a rear end-side portion 84b located on the rear end-side across the second water-penetration reduction portion 94 in the longitudinal direction.

The outer porous layer 85 covers the first to fifth surfaces 60a to 60e. The outer porous layer 85 covers the first surface 60a and the second surface 60b as a result of covering the inner porous layer 81. The length of the outer porous layer 85 in the front-to-rear direction is smaller than the length of the inner porous layer 81 in the front-to-rear direction. The outer porous layer 85 covers only the front end of the element main body 60 and a region of the element main body 60 around the front end, unlike the inner porous layer 81. Thus, the outer porous layer 85 covers a part of the element main body 60 which surrounds the electrodes 64 to 68 included in the detection unit 63. In other words, the outer porous layer 85 covers a part of the element main body 60 which is disposed inside the element chamber 33 and exposed to the measurement-object gas. Thereby, the outer porous layer 85 serves as, for example, a protection layer that reduces the likelihood of moisture and the like included in the measurement-object gas adhering to the element main body 60 and causing cracking of the element main body 60.

The porous layer 80 is composed of, for example, a ceramic porous body, such as an alumina porous body, a zirconia porous body, a spinel porous body, a cordierite porous body, a titania porous body, or a magnesia porous body. In this embodiment, the porous layer 80 is composed of an alumina porous body. The thicknesses of the first inner porous layer 83 and the second inner porous layer 84 may be, for example, 5 µm or more and 40 µm or less. The thickness of the outer porous layer 85 may be, for example, 40 µm or more and 800 µm or less. The porosity of the porous layer 80 is 10% or more. Although the porous layer 80 covers the outer electrode 64 and the gas-to-be-analyzed introduction port 61, the measurement-object gas can pass through the porous layer 80 when the porosity of the porous layer 80 is 10% or more. The porosity of the inner porous layer 81 may be 10% or more and 50% or less. The porosity of the outer porous layer 85 may be 10% or more and 85% or less. The outer porous layer 85 may have a higher porosity than the inner porous layer 81.

The porosity of the inner porous layer 81 is determined by the following method using an image (SEM image) obtained by inspecting the inner porous layer 81 with a scanning electron microscope (SEM). First, the sensor element 20 is cut in the thickness direction of the inner porous layer 81 such that a cross section of the inner porous layer 81 can be inspected. The cross section is buried in a resin and ground in order to prepare an observation sample. An image of the observation cross section of the observation sample is taken with a SEM at a 1000 to 10000-fold magnification in order to obtain an SEM image of the inner porous layer 81. Subsequently, the image is subjected to image analysis. A threshold value is determined on the basis of the brightness distribution included in brightness data of pixels of the image by a discriminant analysis method (Otsu's binarization). On the basis of the threshold value, the pixels of the image are binarized into an object portion and a pore portion. The areas of the object portions and the pore portions are calculated. The ratio of the area of the pore portions to the total area (the total area of the object portions and the pore portions) is calculated as a porosity (unit: %). The porosity of the outer porous layer 85 is also calculated by the same method as described above.

DESCRIPTION OF EMBODIMENTS

The water-penetration reduction portion 90 reduces the capillarity of water through the element main body 60 in the longitudinal direction. In this embodiment, the water-penetration reduction portion 90 includes a first water-penetration reduction portion 91 and a second water-penetration reduction portion 94. The first water-penetration reduction portion 91 is disposed on the first surface 60a, on which the upper connector electrode 71 and the first inner porous layer 83 are disposed. As described above, the first water-penetration reduction portion 91 is disposed on the first surface 60a so as to divide the first inner porous layer 83 into front and rear parts in the longitudinal direction. The first water-penetration reduction portion 91 is arranged closer to the front end of the element main body 60 than the upper connector electrode 71, that is, disposed forward of the upper connector electrode 71. The first water-penetration reduction portion 91 is disposed backward of the outer electrode 64. The first water-penetration reduction portion 91 is disposed backward of any of the electrodes 64 to 68 included in the detection unit 63, in addition to the outer electrode 64 (see FIG. 3). The first water-penetration reduction portion 91 blocks moisture that moves backward inside the front end-side portion 83a by capillarity from passing through the first water-penetration reduction portion 91 and reduces the likelihood of the moisture reaching the upper connector electrode 71. The first water-penetration reduction portion 91 is a gap region of the first surface 60a in which the porous layer 80 is absent. The first water-penetration reduction portion 91 is a region interposed between the rear end of the front end-side portion 83a and the front end of the rear end-side portion 83b. The outer lead wire 75 is exposed to the outside at a part in which the first water-penetration reduction portion 91 is present.

The second water-penetration reduction portion 94 is disposed on the second surface 60b, on which the lower connector electrode 72 and the second inner porous layer 84 are disposed. As described above, the second water-penetration reduction portion 94 is disposed on the second surface 60b so as to divide the second inner porous layer 84 into front and rear parts in the longitudinal direction. The second water-penetration reduction portion 94 is arranged closer to the front end of the element main body 60 than the lower connector electrode 72, that is, disposed forward of the lower connector electrode 72. The second water-penetration reduction portion 94 is disposed backward of the outer electrode 64. The second water-penetration reduction portion 94 is disposed backward of any of the electrodes 64 to 68 included in the detection unit 63, in addition to the outer electrode 64 (see FIG. 3). The second water-penetration reduction portion 94 blocks moisture that moves backward inside the front end-side portion 84a by capillarity from passing through the second water-penetration reduction portion 94 and reduces the likelihood of the moisture reaching the lower connector electrode 72. The second water-penetration reduction portion 94 is a gap region of the second surface 60b in which the porous layer 80 is absent. The second water-penetration reduction portion 94 is a region interposed between the rear end of the front end-side portion 84a and the front end of the rear end-side portion 84b.

The length L of the first and second water-penetration reduction portions 91 and 94 in the longitudinal direction (see FIGS. 4 and 5) is 0.5 mm or more. When the length L is 0.5 mm or more, the likelihood of the moisture passing through the first and second water-penetration reduction portions 91 and 94 can be reduced to a sufficient degree. The length L may be 5 mm or more. The length L may be 25 mm or less or 20 mm or less. Although the first and second water-penetration reduction portions 91 and 94 have the same length L in this embodiment, they may have different lengths L.

The length L of the first and second water-penetration reduction portions 91 and 94 is preferably 1 mm or less. When the length L is relatively small, the area of a part of the side surface (in this embodiment, the first and second surfaces 60a and 60b) of the element main body 60 which is exposed to the outside, that is, the part that is not covered with the porous layer 80, can be reduced. In particular, since an outer lead wire 75 is disposed on the first surface 60a in this embodiment, the outer lead wire 75 is disadvantageously exposed at the part in which the first water-penetration reduction portion 91 is present. Reducing the length L of the first water-penetration reduction portion 91 reduces the area of the part of the outer lead wire 75 which is not protected by the porous layer 80.

Figure 6:
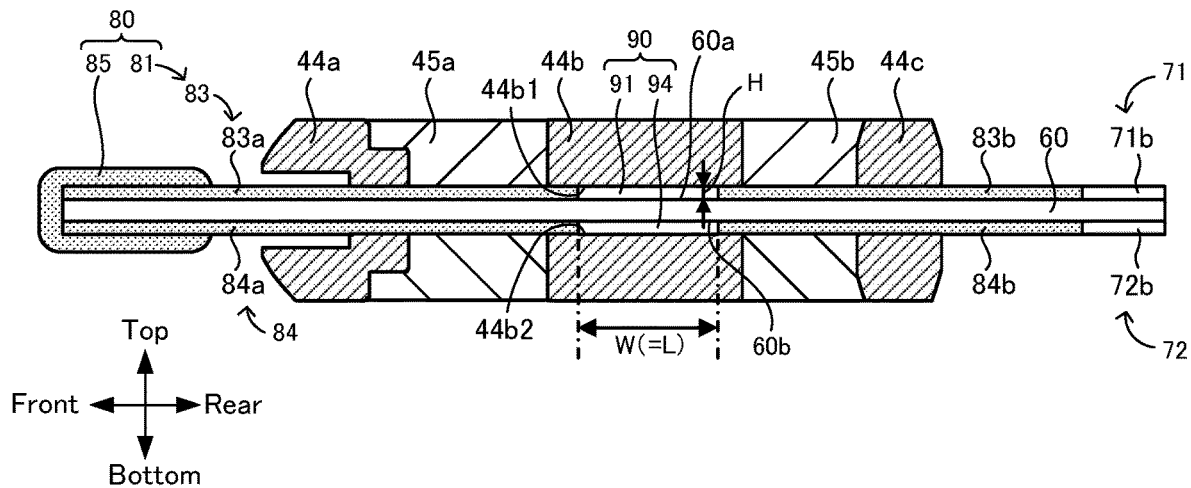
FIG. 6 is a diagram illustrating the positional relationship between an insulator 44b and a water-penetration reduction portion 90.

FIG. 6 is a diagram illustrating the positional relationship between the water-penetration reduction portion 90, the insulators 44a to 44c, and the compacts 45a and 45b. FIG. 6 is a longitudinal cross-sectional view of the gas sensor 10 in which members irrelevant to the description are not illustrated. The first water-penetration reduction portion 91 is arranged such that the overlap length W that is the length of a continuous overlap between the range in which the first water-penetration reduction portion 91 is present in the longitudinal direction of the sensor element 20 (in this embodiment, the front-to-rear direction) and the range in which the inner peripheral surface 44b1 of the insulator 44b is present in the longitudinal direction of the sensor element 20 is 0.5 mm or more. The inner peripheral surface 44b1 of the insulator 44b is a surface of the insulator 44b which faces the first water-penetration reduction portion 91, that is, a surface of the insulator 44b which is exposed to the first water-penetration reduction portion 91. The inner peripheral surface 44b1 is the upper one of the inner peripheral surfaces of the insulator 44b which have a rectangular cross-sectional shape. The overlap length W, which is determined by the positional relationship between the inner peripheral surface 44b1 and the first water-penetration reduction portion 91, corresponds to the length of a continuous part of the first water-penetration reduction portion 91 (gap region) at which the compacts 45a and 45b are not exposed, which is measured in the front-to-rear direction. As illustrated in FIG. 6, in this embodiment, the first water-penetration reduction portion 91 is arranged to be included in the inner peripheral surface 44b1 of the insulator 44b in the front-to-rear direction. More specifically, the first water-penetration reduction portion 91 is arranged such that the region that extends from the front end to the rear end of the first water-penetration reduction portion 91 (the range in which the first water-penetration reduction portion 91 is present in the front-to-rear direction) is included in the region that extends from the front to rear ends of the inner peripheral surface 44b1 of the insulator 44b (the range in which the inner peripheral surface 44b1 is present in the front-to-rear direction). When the above positional relationship is satisfied, Overlap length W=Length L holds for the first water-penetration reduction portion 91. Since the length L is 0.5 mm or more as described above, the overlap length W is also 0.5 mm or more. In this embodiment, the range in which the inner peripheral surface 44b1 is present in the front-to-rear direction is the same as the range in which the insulator 44b is present in the front-to-rear direction. Therefore, the length of a continuous overlap between the range in which the first water-penetration reduction portion 91 is present in the longitudinal direction of the sensor element 20 and the range in which the insulator 44b is present in the longitudinal direction of the sensor element 20 is equal to the overlap length W described above.

Similarly to the first water-penetration reduction portion 91, the second water-penetration reduction portion 94 is arranged such that the overlap length W that is the length of a continuous overlap between the range in which the second water-penetration reduction portion 94 is present in the longitudinal direction of the sensor element 20 (in this embodiment, the front-to-rear direction) and the range in which the inner peripheral surface 44b2 of the insulator 44b is present in the longitudinal direction of the sensor element 20 is 0.5 mm or more. The inner peripheral surface 44b2 of the insulator 44b is a surface of the insulator 44b which faces the second water-penetration reduction portion 94, that is, a surface of the insulator 44b which is exposed to the second water-penetration reduction portion 94. The inner peripheral surface 44b2 is the lower one of the inner peripheral surfaces of the insulator 44b which have a rectangular cross-sectional shape. The overlap length W, which is determined by the positional relationship between the inner peripheral surface 44b2 and the second water-penetration reduction portion 94, corresponds to the length of a continuous part of the second water-penetration reduction portion 94 (gap region) at which the compacts 45a and 45b are not exposed, which is measured in the front-to-rear direction. As illustrated in FIG. 6, in this embodiment, the second water-penetration reduction portion 94 is arranged to be included in the inner peripheral surface 44b2 of the insulator 44b in the front-to-rear direction. More specifically, the second water-penetration reduction portion 94 is arranged such that the region that extends from the front end to the rear end of the second water-penetration reduction portion 94 (the range in which the second water-penetration reduction portion 94 is present in the front-to-rear direction) is included in the region that extends from the front to rear ends of the inner peripheral surface 44b2 of the insulator 44b (the range in which the inner peripheral surface 44b2 is present in the front-to-rear direction). When the above positional relationship is satisfied, Overlap length W=Length L holds for the second water-penetration reduction portion 94. Since the length L is 0.5 mm or more as described above, the overlap length W is also 0.5 mm or more. In this embodiment, the range in which the inner peripheral surface 44b2 is present in the front-to-rear direction is the same as the range in which the insulator 44b is present in the front-to-rear direction. Therefore, the length of a continuous overlap between the range in which the second water-penetration reduction portion 94 is present in the longitudinal direction of the sensor element 20 and the range in which the insulator 44b is present in the longitudinal direction of the sensor element 20 is equal to the overlap length W described above.

Although the overlap length W of the first water-penetration reduction portion 91 and the overlap length W of the second water-penetration reduction portion 94 are equal to each other in this embodiment, they may be different from each other. The overlap length W of the first and second water-penetration reduction portions 91 and 94 may be 5 mm or more and 20 mm or less.

The height H (see FIG. 6) of the first water-penetration reduction portion 91 which is the distance from the side surface (in this embodiment, the first surface 60a) on which the first water-penetration reduction portion 91 is disposed to the inner peripheral surface 44b1 is preferably 50 μm or more. When the height H is large as described above, the capillarity in the gap between the first surface 60a and the inner peripheral surface 44b1 (i.e., inside the first water-penetration reduction portion 91) due to the small distance between the first surface 60a of the element main body 60 on which the first water-penetration reduction portion 91 is disposed and the insulator 44b can be further reduced. For the same reasons, the height H of the second water-penetration reduction portion 94 which is the distance from the side surface (in this embodiment, the second surface 60b) on which the second water-penetration reduction portion 94 is disposed to the inner peripheral surface 44b2 is preferably 50 μm or more. The height H of the first and second water-penetration reduction portions 91 and 94 is more preferably 100 μm or more. The height H of the first and second water-penetration reduction portions 91 and 94 may be 500 μm or less. Although the height H of the first water-penetration reduction portion 91 and the height H of the second water-penetration reduction portion 94 are equal to each other in this embodiment, they may be different from each other.

Although the inner peripheral surface 44b1 and the upper surface of the first inner porous layer 83 are in contact with each other and the height H of the first water-penetration reduction portion 91 is equal to the thickness of the first inner porous layer 83 in FIG. 6, the inner peripheral surface 44b1 and the upper surface of the first inner porous layer 83 may be arranged to separate from each other in the top-to-bottom direction. When the inner peripheral surface 44b1 and the upper surface of the first inner porous layer 83 are arranged to separate from each other, the contact between the inner peripheral surface 44b1 and the upper surface of the first inner porous layer 83 which occurs when, for example, they become expanded by heat or the gas sensor 10 is shaken can be reduced and, consequently, the likelihood of at least one of the insulator 44b and the sensor element 20 becoming broken can be reduced. In the case where the inner peripheral surface 44b1 and the upper surface of the first inner porous layer 83 are arranged to separate from each other, the height H of the first water-penetration reduction portion 91 may be equal to the total sum of the thickness of the first inner porous layer 83 and the separation distance between the inner peripheral surface 44b1 and the upper surface of the first inner porous layer 83 in the top-to-bottom direction. Similarly, although the inner peripheral surface 44b2 and the lower surface of the second inner porous layer 84 are in contact with each other in FIG. 6, they may be arranged to separate from each other in the top-to-bottom direction.

The method for producing the gas sensor 10 is described below. First, the method for producing the sensor element 20 is described. In the production of the sensor element 20, first, a plurality of (in this embodiment, six) unbaked ceramic green sheets that correspond to the element main body 60 are prepared. In each of the green sheets, as needed, notches, through-holes, grooves, and the like are formed by punching or the like, and electrodes and wire patterns are formed by screen printing. In addition, unbaked porous layers that are to be formed into the first inner porous layer 83 and the second inner porous layer 84 after baking are formed on the surfaces of the green sheets which correspond to the first and second surfaces 60a and 60b by screen printing. The unbaked porous layers are provided with gap regions formed therein such that the first and second water-penetration reduction portions 91 and 94 are formed. Subsequently, the green sheets are stacked on top of one another. The green sheets stacked on top of one another are an unbaked element main body that is to be formed into the element main body after baking and include unbaked porous layers. The unbaked element main body is baked to form the element main body 60 including the first and second inner porous layers 83 and 84 and the first and second water-penetration reduction portions 91 and 94. Subsequently, the outer porous layer 85 is formed by plasma spraying. Hereby, the sensor element 20 is prepared. For producing the porous layer 80, gel casting, dipping, and the like can be used in addition to screen printing and plasma spraying.

The gas sensor 10 that includes the sensor element 20 is produced. First, the sensor element 20 is inserted into the cylindrical body 41 so as to penetrate the cylindrical body 41 in the axial direction. Subsequently, the insulator 44a, the compact 45a, the insulator 44b, the compact 45b, the insulator 44c, and the metal ring 46 are disposed in the gap between the inner peripheral surface of the cylindrical body 41 and the sensor element 20 in this order. Then, the metal ring 46 is pressed in order to compress the compacts 45a and 45b. While the compacts 45a and 45b are compressed, the diameter reduction portions 43c and 43d are formed. Hereby, the element-sealing member 40 is produced, and the gap between the inner peripheral surface of the cylindrical body 41 and the sensor element 20 is sealed. The protective cover 30 is welded to the element-sealing member 40, and the nut 47 is attached to the element-sealing member 40. Hereby, the assembly 15 is produced. Lead wires 55 attached to a rubber stopper 57 so as to penetrate the rubber stopper 57 and a connector 50 connected to the lead wires 55 are prepared. The connector 50 is connected to the rear end-side part of the sensor element 20. Subsequently, the external cylinder 48 is fixed to the main fitting 42 by welding. Hereby, the gas sensor 10 is produced.

An example of the application of the gas sensor 10 is described below. When the measurement-object gas flows inside the pipe 58 while the gas sensor 10 is attached to the pipe 58 as illustrated in FIG. 1, the measurement-object gas passes through the inside of the protective cover 30 and enters the element chamber 33. Consequently, the front end-side part of the sensor element 20 is exposed to the measurement-object gas. Upon the measurement-object gas passing through the porous layer 80, reaching the outer electrode 64, and reaching the inside of the sensor element 20 through the gas-to-be-analyzed introduction port 61, the detection unit 63 generates an electrical signal reflective of the NOx concentration in the measurement-object gas, as described above. The electrical signal is drawn through the upper and lower connector electrodes 71 and 72. The NOx concentration can be determined on the basis of the electrical signal.

The measurement-object gas may contain moisture, which may move inside the porous layer 80 by capillarity. If the moisture reaches the upper and lower connector electrodes 71 and 72, which are exposed to the outside, the water and the components dissolved in the water, such as sulfuric acid, may cause rusting and corrosion of the upper and lower connector electrodes 71 and 72 and a short circuit between some of the upper and lower connector electrodes 71 and 72 which are adjacent to one another. However, in this embodiment, even when the moisture contained in the measurement-object gas moves inside the porous layer 80 (in particular, inside the first inner porous layer 83 and the second inner porous layer 84) toward the rear end-side part of the element main body 60 by capillarity, the moisture reaches the first water-penetration reduction portion 91 or the second water-penetration reduction portion 94 before reaching the upper and lower connector electrodes 71 and 72. Since the first water-penetration reduction portion 91 is a gap region that is a space in which the porous layer is absent, the capillarity of water in the longitudinal direction of the element main body 60 is reduced. In addition, since the length L of the first water-penetration reduction portion 91 in the longitudinal direction is 0.5 mm or more, the likelihood of moisture passing through the first water-penetration reduction portion 91 can be reduced to a sufficient degree. By the above mechanisms, the first water-penetration reduction portion 91 reduces the likelihood of the moisture passing through the first water-penetration reduction portion 91 from the front end-side portion 83a side.

Figure 7:
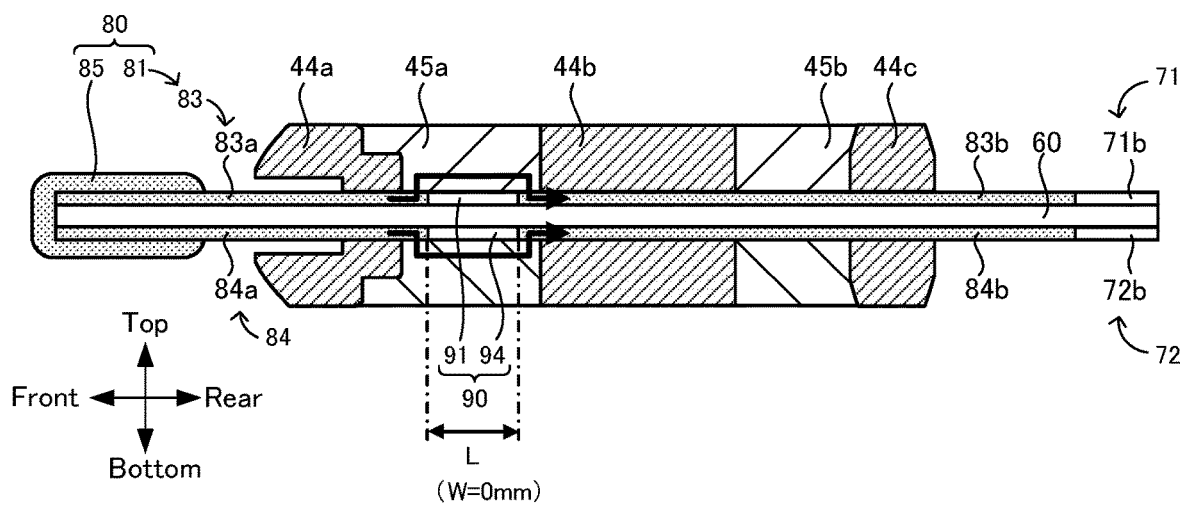
FIG. 7 is a diagram illustrating the placement of a water-penetration reduction portion 90 when the overlap length W=0 mm.

Since the length W of the overlap between the first water-penetration reduction portion 91 and the insulator 44b is 0.5 mm or more, the likelihood of the moisture bypassing the first water-penetration reduction portion 91 and moving into the rear end-side part of the sensor element 20 as a result of passing through the compacts 45a and 45b can be reduced to a sufficient degree. For example, a case where the first and second water-penetration reduction portions 91 and 94 are disposed at only the position that is the same, in the longitudinal direction of the sensor element 20, as the position at which the compact 45a is disposed, that is, the overlap length W is 0 mm, as illustrated in FIG. 7 is taken as a comparative example. In this case, while the moisture cannot pass through the first water-penetration reduction portion 91 by capillarity, the moisture can move inside the compact 45a since the compact 45a absorbs water. Consequently, the moisture may bypass the first water-penetration reduction portion 91 as a result of passing through the compact 45a and move into the rear end-side part across the first water-penetration reduction portion 91 (see the thick arrow in FIG. 7). In contrast, in the sensor element 20 according to this embodiment, the first water-penetration reduction portion 91 is arranged as illustrated in FIG. 6, and the overlap length W is 0.5 mm or more. In the part of the overlap length W (overlap part), the compact 45a is not exposed at the first water-penetration reduction portion 91, and the moisture hardly passes through the insulator 44b because the insulator 44b is dense. Therefore, the bypass of the moisture as illustrated in FIG. 7 is not likely to occur. Furthermore, since the overlap length W is 0.5 mm or more, the region that inhibits the moisture from bypassing the first water-penetration reduction portion 91 is present over a sufficiently large distance and, accordingly, the movement of the moisture due to the bypass can be reduced to a sufficient degree.

By the above-described mechanisms, the first water-penetration reduction portion 91 reduces the likelihood of the moisture that moves inside the porous layer 80 (in particular, the front end-side portion 83a) passing through the first water-penetration reduction portion 91 and bypassing the first water-penetration reduction portion 91 as a result of passing through the compacts 45a and 45b. Consequently, in the gas sensor 10, the likelihood of the moisture moving into the rear end-side part of the sensor element 20 across the first water-penetration reduction portion 91 and reaching the upper connector electrode 71 can be reduced.

Therefore, in the sensor element 20, the above-described trouble caused by the water adhering to the upper connector electrode 71 may be reduced.

In the same manner as described above, since the length W of the overlap between the second water-penetration reduction portion 94 and the insulator 44b is 0.5 mm or more, the second water-penetration reduction portion 94 reduces the likelihood of the moisture that moves inside the porous layer 80 (in particular, the front end-side portion 84a) passing through the second water-penetration reduction portion 94 and bypassing the second water-penetration reduction portion 94 as a result of passing through the compacts 45a and 45b. Consequently, in the gas sensor 10, the likelihood of the moisture moving into the rear end-side part of the sensor element 20 across the second water-penetration reduction portion 94 and reaching the lower connector electrode 72 can be reduced. Therefore, in the sensor element 20, the above-described trouble caused by the water adhering to the lower connector electrode 72 may be reduced.

The correspondences between the elements constituting this embodiment and the elements constituting the present invention are explicitly described below: the sensor element 20 in this embodiment corresponds to the sensor element in the present invention; the cylindrical body 41 corresponds to the cylindrical body, the compacts 45a and 45b correspond to the compacts, the insulators 44a to 44c correspond to the dense bodies; the element main body 60 corresponds to the element main body; the detection unit 63 corresponds to the detection unit; the connector electrodes 71a to 71d and 72a to 72d correspond to the connector electrodes; the first surface 60a and the second surface 60b correspond to the side surface on which the connector electrodes are disposed; the porous layer 80 corresponds to the porous layer; the first and second water-penetration reduction portions 91 and 94 each correspond to the water-penetration reduction portion; the outer lead wire 75 corresponds to the outer lead portion; the outer electrode 64 corresponds to the outer electrode; the first surface 60a corresponds to the first side surface; and the second surface 60b corresponds to the second side surface.

Since the sensor element 20 according to this embodiment described above in detail includes the first water-penetration reduction portion 91 disposed on any of the one or more side surfaces (in this embodiment, the first surface 60a) of the element main body 60, the likelihood of the moisture moving into the rear end-side part of the sensor element 20 across the first water-penetration reduction portion 91 and reaching the upper connector electrodes 71a to 71d can be reduced. In the same manner as above, since the sensor element 20 includes the second water-penetration reduction portion 94 disposed on any of the one or more side surfaces (in this embodiment, the second surface 60b) of the element main body 60, the likelihood of the moisture moving into the rear end-side part of the sensor element 20 across the second water-penetration reduction portion 94 and reaching the lower connector electrodes 72a to 72d can also be reduced.

Since the length L of the first and second water-penetration reduction portions 91 and 94 is 1 mm or less, that is, relatively small, the area of parts of the side surfaces (in this embodiment, the first and second surfaces 60a and 60b) of the element main body 60 which are exposed to the outside (the parts that are not covered with the porous layer 80) can be reduced.

Furthermore, since the height H of the first and second water-penetration reduction portions 91 and 94 is 50 μm or more, the capillarity in the gap between the first surface 60a and the inner peripheral surface 44b1 and the gap between the second surface 60b and the inner peripheral surface 44b2 due to the small distance between the side surfaces (in this embodiment, the first and second surfaces 60a and 60b) of the element main body 60 on which the first and second water-penetration reduction portions 91 and 94 are disposed and the insulator 44b can be further reduced.

The sensor element 20 includes an outer lead wire 75 that is disposed on the side surface (in this embodiment, the first surface 60a) on which the upper connector electrode 71 is disposed and that provides electrical conduction between any of the electrodes (in this embodiment, the outer electrode 64) included in the detection unit 63 and the upper connector electrode 71b. The porous layer 80 (in particular, the first inner porous layer 83) covers at least a part of the outer lead wire 75. Consequently, at least a part of the outer lead wire 75 can be protected by the porous layer 80. In the case where the outer lead wire 75 is protected by the porous layer 80, the porous layer (in this embodiment, the first inner porous layer 83) is likely to be formed at a position close to the lower connector electrode 71b. In such a case, it is meaningful to reduce the likelihood of the moisture passing through the first inner porous layer 83 and reaching the lower connector electrode 71b by using the first water-penetration reduction portion 91.

The present disclosure is not limited to the above-described embodiment, and can be carried out by various modes as long as they belong to the technical scope of the disclosure.

Although the gas sensor 10 includes three insulators (insulators 44a to 44c) and two compacts (compacts 45a and 45b) in the above-described embodiment, the present invention is not limited to this. The gas sensor 10 includes one or more insulators and one or more compacts. Although the insulators 44a to 44c are described as an example of the dense bodies in the above-described embodiment, the present invention is not limited to this. One or more of the insulators 44a to 44c may be a dense body having a porosity of less than 10%. A dense body having a porosity of less than 10% hardly allows moisture to pass therethrough and reduces the above-described movement of the moisture, which occurs as a result of the moisture bypassing the water-penetration reduction portion 90, to a sufficient degree. The porosity of the dense bodies may be less than 5%. The porosity of the dense bodies is determined using a SEM as in the measurement of the porosity of the inner porous layer 81.

Although the first and second water-penetration reduction portions 91 and 94 are arranged to overlap the insulator 44b in the front-to-rear direction in the above-described embodiment, the present invention is not limited to this. For example, the first and second water-penetration reduction portions 91 and 94 may be arranged to overlap the insulator 44a or the insulator 44c in the front-to-rear direction. However, in the case where the first water-penetration reduction portion 91 is arranged to overlap only one of the insulators included in the gas sensor 10 which is closest to the front end (in the above-described embodiment, the insulator 44a), gaseous moisture contained in the measurement-object gas may disadvantageously pass through the gap between the first water-penetration reduction portion 91 and the insulator 44a and move into the rear end-side part of the sensor element 20 across the first water-penetration reduction portion 91. In the case where the first water-penetration reduction portion 91 is arranged to overlap only one of the insulators included in the gas sensor 10 which is closest to the rear end (in the above-described embodiment, the insulator 44c), the first water-penetration reduction portion 91 is arranged relatively close to the upper connector electrode 71. In such a case, while the first water-penetration reduction portion 91 is capable of reducing the likelihood of liquid moisture moving toward the upper connector electrode 71 by capillarity, part of the liquid moisture may vaporize at the forward of the first water-penetration reduction portion 91 and the resulting gaseous moisture may disadvantageously pass through the gap between the first water-penetration reduction portion 91 and the insulator 44c, move into the rear end-side part of the sensor element 20 across the first water-penetration reduction portion 91, and reach the upper connector electrode 71. For the above reasons, in the case where the gas sensor 10 includes two or more insulators, the first water-penetration reduction portion 91 is preferably arranged to overlap an insulator other than the insulator closest to the front end. In the case where the gas sensor 10 includes three or more insulators, the first water-penetration reduction portion 91 is preferably arranged to overlap an insulator other than the insulator closest to the front end or the insulator closest to the rear end.

In the above-described embodiment, the sensor element 20 does not necessarily include the second inner porous layer 84 and the second surface 60b is not necessarily covered with the porous layer 80. In such a case, the sensor element 20 does not necessarily include the second water-penetration reduction portion 94. The water-penetration reduction portion may be disposed on at least one of the side surfaces of the element main body (in the above-described embodiment, the first to fourth surfaces 60a to 60d) on which the connector electrodes and the porous protection layer are disposed (in the above-described embodiment, the first and second surfaces 60a and 60b). This reduces the likelihood of the moisture reaching the connector electrodes at least on the side surface on which the water-penetration reduction portion is disposed.

Although the first inner porous layer 83 covers the region that extends from the front to rear ends of the first surface 60a except the region in which the first water-penetration reduction portion 91 and the upper connector electrode 71 are present in the above-described embodiment, the present invention is not limited to this. For example, the first inner porous layer 83 may cover a region that extends from the front end of the first surface 60a to the front end-side ends of the upper connector electrodes 71a to 71d except the region in which the first water-penetration reduction portion 91 is present. Alternatively, the first inner porous layer 83 may cover at least a region that extends from the front end of the first surface 60a to the rear of the first water-penetration reduction portion 91 except the region in which the first water-penetration reduction portion 91 is present. The same applies to the second inner porous layer 84.

Although the element main body 60 has a rectangular cuboid shape in the above-described embodiment, the present invention is not limited to this. For example, the element main body 60 may have a hollow cylindrical shape or a solid cylindrical shape. In such a case, the element main body 60 has one side surface.

EXAMPLES

Example cases where a specific sensor element was prepared are described below as Examples. Experimental examples 1 to 4 correspond to Examples of the present invention, while Experimental examples 5 to 7 correspond to Comparative examples. Note that the present invention is not limited by Examples below.

Experimental Example 1

Figure 8:
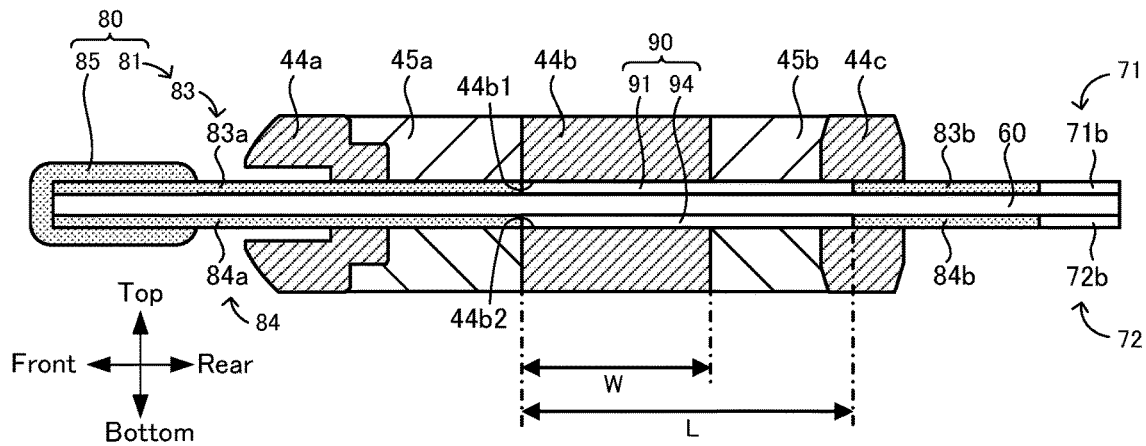
FIG. 8 is a diagram illustrating a gas sensor 10 prepared in Experimental example 1.

In Experimental example 1, a sensor element that was the same as the sensor element 20 illustrated in FIGS. 2 to 5 was prepared, and a gas sensor 10 that included this sensor element was prepared. Note that, in Experimental example 1, the positional relationship between the insulator 44b and the water-penetration reduction portion 90 was changed from the above-described embodiment illustrated in FIG. 6 as illustrated in FIG. 8. The sensor element 20 of the Experimental example 1 was prepared in the following manner. First, zirconia particles containing 4 mol % yttria serving as a stabilizer were mixed with an organic binder and an organic solvent. The resulting mixture was formed into six ceramic green sheets by tape casting. Patterns of electrodes and the like were printed in each of the green sheets. In addition, unbaked porous layers that were to be formed into the first inner porous layer 83 and the second inner porous layer 84 after baking were formed by screen printing. The unbaked porous layers were formed such that the first and second water-penetration reduction portions 91 and 94 were able to be formed. The unbaked porous layers were composed of a slurry prepared by mixing a raw-material powder (an alumina powder), a binder solution (polyvinyl acetal and butyl carbitol), a solvent (acetone), and a pore-forming material with one another. Subsequently, the six green sheets were stacked on top of one another and baked in order to prepare the element main body 60 including the first and second inner porous layers 83 and 84. Hereby, the sensor element 20 of Experimental example 1 was prepared. The dimensions of the element main body 60 were 67.5 mm long, 4.25 mm wide, and 1.45 mm thick. The first and second inner porous layers 83 and 84 had a thickness of 20 μm and a porosity of 30%.

In the preparation of the gas sensor 10 of Experimental example 1, the insulators 44a to 44c were sintered ceramic bodies composed of alumina. The lengths of the insulators 44a, 44b, and 44c in the axial direction were 8 mm, 10 mm, and 4.5 mm, respectively. The porosity of the insulators 44a to 44c determined using a SEM image was less than 1%. The compacts 45a and 45b were formed by molding a talc powder. The amount of the talc powder used was adjusted such that an adequate sealing load was applied to the compacts 45a and 45b inside the cylindrical body 41 in the front-to-rear direction. The length of the compact 45a in the axial direction which was measured after sealing was 6 mm. The length of the compact 45b in the axial direction which was measured after sealing was 7 mm. The separation distance between the insulators 44a to 44c and the porous layer 80 in the top-to-bottom direction was 100 μm. The length L of the first and second water-penetration reduction portions 91 and 94 illustrated in FIG. 8 was 20 mm. In Experimental example 1, the position of the front ends of the first and second water-penetration reduction portions 91 and 94 was the same as the position of the front ends of the inner peripheral surfaces 44b1 and 44b2 of the insulator 44b. In Experimental example 1, the front ends of the first and second water-penetration reduction portions 91 and 94 were located 29 mm from the front end of the element main body 60. As illustrated in FIG. 8, the first and second water-penetration reduction portions 91 and 94 were arranged to overlap the insulators 44b and 44c. The overlap length W, which is the length of a continuous overlap, determined on the basis of the positional relationship between the water-penetration reduction portions and the insulator 44b, which was arranged to overlap the water-penetration reduction portions over a larger distance, was 10 mm. The height H of the first and second water-penetration reduction portions 91 and 94 was 120 μm (the total sum of the separation distance (100 μm) between the insulators 44a to 44c and the porous layer 80 in the top-to-bottom direction and the thickness (20 μm) of the first and second inner porous layers 83 and 84). In Experimental examples 2 to 6 below, the height H was set to the same value as in Experimental example 1.

Experimental Example 2

In Experimental example 2, a gas sensor 10 that was the same as the gas sensor 10 prepared in Experimental example 1 was prepared, except that the shape of the first and second inner porous layers 83 and 84 was changed such that the insulator 44b and the water-penetration reduction portion 90 had the positional relationship illustrated in FIG. 6 in the front-to-rear direction. In Experimental example 2, the first and second water-penetration reduction portions 91 and 94 were included in the insulator 44b in the front-to-rear direction as illustrated in FIG. 6, and the overlap length W was 5 mm (=L). In Experimental example 2, the front ends of the first and second water-penetration reduction portions 91 and 94 were located 31 mm from the front end of the element main body 60.

Experimental Examples 3 to 5

Figure 9:
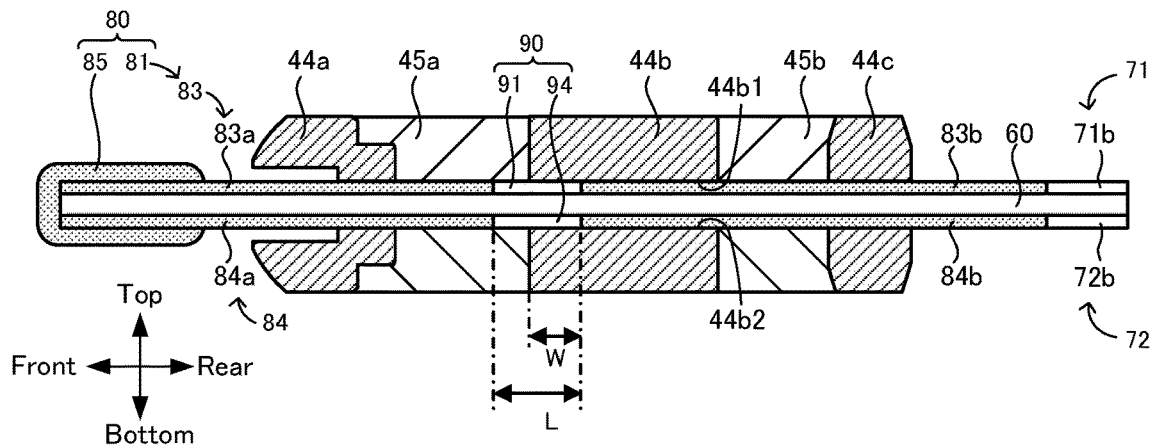
FIG. 9 is a diagram illustrating a gas sensor 10 prepared in Experimental examples 3 to 5.

In Experimental examples 3 to 5, a gas sensor 10 that was the same as the gas sensor 10 prepared in Experimental example 1 was prepared, except that the shape of the first and second inner porous layers 83 and 84 was changed such that the insulator 44b and the water-penetration reduction portion 90 had the positional relationship illustrated in FIG. 9 in the front-to-rear direction. In Experimental examples 3 to 5, the length L of the first and second water-penetration reduction portions 91 and 94 was set to 5 mm. As illustrated in FIG. 9, the rear end-side parts of the first and second water-penetration reduction portions 91 and 94 overlapped the insulator 44b in the front-to-rear direction, and the overlap length W was 3 mm, 0.5 mm, and 0.3 mm in Experimental examples 3, 4, and 5, respectively. The distance from the front end of the element main body 60 to the front ends of the first and second water-penetration reduction portions 91 and 94 was 27 mm, 24.5 mm, and 24.3 mm in Experimental examples 3, 4, and 5, respectively.

Experimental Example 6

In Experimental example 6, a gas sensor 10 that was the same as the gas sensor 10 prepared in Experimental example 1 was prepared, except that the shape of the first and second inner porous layers 83 and 84 was changed such that the insulator 44b and the water-penetration reduction portion 90 had the positional relationship illustrated in FIG. 7 in the front-to-rear direction. In Experimental example 6, the length L of the first and second water-penetration reduction portions 91 and 94 was set to 5 mm, and the overlap length W was 0 mm. In Experimental example 6, the front ends of the first and second water-penetration reduction portions 91 and 94 were located 23.5 mm from the front end of the element main body 60.

Experimental Example 7

In Experimental example 7, a gas sensor 10 was prepared as in Experimental example 1, except that the first and second water-penetration reduction portions 91 and 94 were not formed. That is, in Experimental example 7, the first and second inner porous layers 83 and 84 were not divided in the front-to-rear direction and covered the entirety of the first and second surfaces 60a and 60b except the regions in which the upper and lower connector electrodes 71 and 72 were disposed. The length L of the water-penetration reduction portions and the overlap length W were 0 mm.

[Liquid Penetration Experimental]

Each of the gas sensors 10 prepared in Experimental examples 1 to 7 was tested in order to determine the amount of liquid that penetrated the rear end-side part of the element main body 60 by capillarity when the front end-side part of the element main body 60 was immersed in the liquid. First, while the gas sensor 10 was held such that the longitudinal direction (the front-to-rear direction) of the gas sensor 10 was parallel to the vertical direction, a part of the gas sensor 10 which extended from the front end of the gas sensor 10 to a predetermined immersion position was immersed into a red-check solution. The predetermined immersion position was set to a position 20 mm from the front end (the fifth surface 60e) of the element main body 60 of the sensor element 20 toward the rear end. While the gas sensor was immersed in the red-check solution, the gas sensor was left to stand for 150 hours. Subsequently, the distance the red-check solution penetrated from the immersion position toward the rear end was measured visually as a penetration distance. The penetration distance indicates the distance the red-check solution moved from the immersion position toward the rear end of the element main body 60 inside the first and second inner porous layers 83 and 84 by capillarity. An evaluation grade of Excellent (A) was given when the penetration distance measured after a lapse of 150 hours was less than 15 mm. An evaluation grade of Failure (F) was given when the penetration distance measured after a lapse of 150 hours was 15 mm or more. The red-check solution used was "R-3B(NT) PLUS" produced by Eishin Kagaku Co., Ltd. The red-check solution included 40 to 60 wt % hydrocarbon oil, 10 to 20 wt % plastic solvent, 1 to 20 wt % glycol ether, 12 to 50 wt % non-ionic surfactant, and 1 to 5 wt % oil-soluble azo red dye. The red-check solution had a density of 0.86 g/cm$^3$ at 20° C., which was lower than the density of water.

Figure 10:
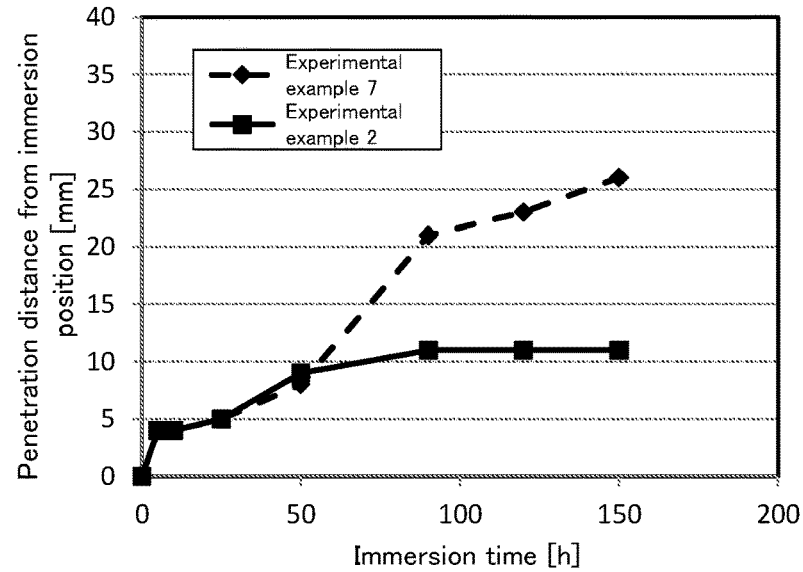
FIG. 10 is a graph illustrating changes in penetration distance with time which were measured in liquid penetration tests conducted in Experimental examples 2 and 7.

Table 1 summarizes the overlap length W, the length L, and the results of evaluation of the liquid penetration test in each of Experimental examples 1 to 7. FIG. 10 is a graph illustrating changes in penetration distance with time which were measured in the liquid penetration tests conducted in Experimental examples 2 and 7.

TABLE 1

|  | Overlap length W [mm] | Length L of water-penetration reduction portion [mm] | Liquid penetration test |
| --- | --- | --- | --- |
| Experimental example 1 | 10 | 20 | A |
| Experimental example 2 | 5 | 5 | A |
| Experimental example 3 | 3 | 5 | A |
| Experimental example 4 | 0.5 | 5 | A |
| Experimental example 5 | 0.3 | 5 | F |

TABLE 1-continued

| | Overlap length W [mm] | Length L of water-penetration reduction portion [mm] | Liquid penetration test |
|---|---|---|---|
| Experimental example 6 | 0 | 5 | F |
| Experimental example 7 | 0 | 0 | F |

The results illustrated in FIG. 10 show that, in Experimental example 7 where the first and second water-penetration reduction portions 91 and 94 were absent, the penetration distance increased with time. This confirms that the red-check solution moved inside the first and second inner porous layers 83 and 84 toward the rear of the sensor element 20 by capillarity. In contrast, in Experimental example 2 where the first and second water-penetration reduction portions 91 and 94 were present and the overlap length W was 0.5 mm or more, the red-check solution reached a position corresponding to a penetration distance of 11 mm (=the position 31 mm from the front end of the element main body 60) that was the position of the front ends of the first and second water-penetration reduction portions 91 and 94. This confirms that, in Experimental example 2, the first and second water-penetration reduction portions 91 and 94 blocked the red-check solution from moving backward.

The results described in Table 1 show that, in Experimental examples 1 to 4 where the overlap length W was 0.5 mm or more, the results of the liquid penetration test were evaluated as Excellent. In contrast, in Experimental examples 5 to 7 where the overlap length W was less than 0.5 mm, the results of the liquid penetration test were evaluated as Failure. This confirms that, when the overlap length W is 0.5 mm or more, the movement of the moisture can be reduced by the first and second water-penetration reduction portions 91 and 94 to a sufficient degree. The results obtained in Experimental examples 5 and 6 confirm that, in the case where the overlap length W is less than 0.5 mm, the movement of the moisture cannot be suppressed to a sufficient degree even when the length L is large. This is presumably because the moisture bypasses the first and second water-penetration reduction portions 91 and 94 as a result of passing through the compacts and moves toward the rear.

What is claimed is:

1. A gas sensor comprising:
a sensor element; a cylindrical body made of a metal, the cylindrical body having a through-hole through which the sensor element penetrates an inside of the cylindrical body in an axial direction of the cylindrical body; one or more compacts disposed in the through-hole, the one or more compacts filling a gap between an inner peripheral surface of the through-hole and the sensor element; and one or more hollow columnar dense bodies having a porosity of less than 10%, the one or more dense bodies being disposed in the through-hole, the one or more dense bodies being penetrated by the sensor element, the one or more dense bodies pressing the one or more compacts in the axial direction,
the sensor element including
a long-length element main body including front and rear ends and one or more side surfaces, the front and rear ends being ends of the element main body in a longitudinal direction of the element main body, the one or more side surfaces being surfaces extending in the longitudinal direction;
a detection unit including a plurality of electrodes disposed in the front end-side part of the element main body, the detection unit detecting the specific gas concentration in a measurement-object gas;
one or more connector electrodes disposed on the rear end-side part of any of the one or more side surfaces, the one or more connector electrodes used for in electrical conduction with the outside;
a porous layer that covers at least the front end-side part of the one or more side surfaces on which the one or more connector electrodes are disposed, the porous layer having a porosity of 10% or more, and
a water-penetration reduction portion disposed on the one or more side surface so as to divide the porous layer in the longitudinal direction, the water-penetration reduction portion being located closer to the front end than the one or more connector electrodes, an overlap length W that is the length of a continuous overlap between a range in which the water-penetration reduction portion is present in the longitudinal direction and a range in which inner peripheral surfaces of the one or more dense bodies are present in the longitudinal direction being 0.5 mm or more, the water-penetration reduction portion being a gap region in which the porous layer is absent, the water-penetration reduction portion reducing the capillarity of water in the longitudinal direction.

2. The gas sensor according to claim 1,
wherein the length L of the water-penetration reduction portion in the longitudinal direction is 1 mm or less.

3. The gas sensor according to claim 1,
wherein a height H of the water-penetration reduction portion, the height H being the distance from the one of the one or more side surfaces to an inner peripheral surface of one of the one or more dense bodies, is 50 μm or more.

4. The gas sensor according to claim 1,
wherein the sensor element further includes an outer lead portion disposed on a side surface of the one or more side surfaces on which the one or more connector electrodes are disposed, the outer lead portion providing electrical conduction between any of the plurality of electrodes and the one or more connector electrodes, and
wherein the porous layer covers at least a part of the outer lead portion.

5. The gas sensor according to claim 1,
wherein the porous layer covers at least a region of the side surface on which the one or more connector electrodes are disposed, the region extending from the front end of the side surface to the front end-side edges of the one or more connector electrodes, the region excluding a region in which the water-penetration reduction portion is present.

6. The gas sensor according to claim 1,
wherein the element main body has a rectangular cuboid shape with four side surfaces that are the one or more side surfaces extending in the longitudinal direction,
wherein the one or more connector electrodes are disposed on each of first and second side surfaces of the four side surfaces, the first and second side surfaces facing each other, wherein the porous layer covers the first and second side surfaces, and wherein the water-penetration reduction portion is disposed on each of the first and second side surfaces.

* * * * *